(12) United States Patent
Hatori et al.

(10) Patent No.: US 6,302,841 B1
(45) Date of Patent: Oct. 16, 2001

(54) BENDABLE TUBE OF ENDOSCOPE

(75) Inventors: Tsuruo Hatori, Sagamihara; Hideki Tsujiya, Hachioji, both of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/397,892

(22) Filed: Sep. 17, 1999

(51) Int. Cl.[7] .................................................. A61B 1/005
(52) U.S. Cl. ............................................................. 600/142
(58) Field of Search .................................... 600/141, 142; 356/241.4

(56) References Cited

U.S. PATENT DOCUMENTS 5,178,129  1/1993  Chikama et al. .

FOREIGN PATENT DOCUMENTS 60-187702  12/1985  (JP) .

3-37031A  * 2/1989  (JP) ...................................... 600/142

* cited by examiner

*Primary Examiner*—John Mulcahy
(74) *Attorney, Agent, or Firm*—Frishauf, Holtz, Goodman, Langer & Chick, P.C.

(57) ABSTRACT

In a bendable tube of an endoscope, a plurality of joint rings each having a rotational axis perpendicular to a direction of bending of an insertion section of the endoscope are arranged in a longitudinal direction of the insertion section. A pair of connection tongue portions provided to project in a longitudinal direction of the joint rings are rotatably connected by means of a shaft member. An end face of a small-diameter portion of the shaft member, which comprises the small-diameter portion and a large-diameter portion, is welded to one of the tongue portions through a rotary shaft hole, which is formed in the other tongue portion and has a diameter slightly greater than a diameter of the small-diameter portion.

10 Claims, 4 Drawing Sheets

BENDABLE TUBE OF ENDOSCOPE

BACKGROUND OF THE INVENTION

The present invention relates to a bendable tube of an endoscope, which bendable tube is constituted by linearly arranging a plurality of joint rings and pivotally connecting adjacent ones of them by means of shaft pins.

In an insertion section of an endoscope, a bendable tube is provided between a resilient tube and a distal portion. The bendable tube is forcibly bent by a pulling operation performed on the proximal-end side by means of manipulation wire elements. In an ordinary bendable tube, a plurality of joint rings are linearly arranged in the longitudinal direction of the insertion section of the endoscope and, with ear portions of adjacent joint rings overlapped, the overlapped ear portions are pivotally connected by means of shaft pins (see Jpn. U.M. Appln. KOKAI Publication No. 60-187702).

FIGS. 9 and 10 show the structure of a conventional bendable tube. As is shown in FIG. 9, a bendable tube 50 is constituted such that a plurality of joint rings 51 are linearly arranged in the longitudinal direction of an insertion section and, with mutually opposed ear portions 52 and 53 of adjacent joint rings 51 overlapped, rivet-like shaft pins 56 are passed through insertion holes 54 and 55 formed in the ear portions 52 and 53. One end of each shaft pin 56 is caulked on one of opposed ear portions, 52. Thus, adjacent joint rings 51 are pivotally connected.

Needless to say, the width of each ear portion 52, 53 should be as small as possible in order to reduce the diameter of the bendable tube 50 and to reduce as much as possible the distance of that portion of the pivotal connection section, which projects toward the center of the inner cavity of the bendable tube 50. However, since the insertion holes 54 and 55 for insertion of the shaft pins 56 need to be provided and the mechanical strength for caulking has to be maintained, it is necessary that the ear portions 52, 53 have certain widths.

In an example shown in FIG. 10, the width of the ear portion 52 located inside is made different from that of the ear portion 53 located outside in order to achieve reduction in diameter of the bendable tube 50 while maintaining maximum widths of the ear portions 52 and 53 and to reduce as much as possible the distance of projection of the ear portion 52, 53 toward the center of the inner cavity of the bendable tube 50. The width of the ear portion 53 located outside is made less than that of the ear portion 52 located inside, and the insertion holes 54 and 55 are modified stepwise accordingly.

In this case, however, when the joint rings are pivotally connected, the ear portions of the adjacent joint rings of the bendable tube are overlapped, the rivet-type shaft pin is passed through the insertion holes of the overlapped ear portions, and one end of the shaft pin is caulked on one of the overlapped ear portions. Accordingly, the insertion holes need to be formed in both the overlapped ear portions and each insertion hole needs to be formed to have a certain size. Furthermore, the width of the ear portion needs to be determined in accordance with the size of the insertion hole. Although the width of the outside ear portion should preferably be made less than that of the inside ear portion, the reduction in width of the outside ear portion is limited. In the prior art, it is difficult to further reduce the width of the ear portion and to make the location of the structure of the pivotal connection closer to the inner surface of the cavity in the bendable tube.

In the conventional structure, unless a certain thickness is maintained for both the ear portions for pivotally connecting the adjacent joint rings, coupling strength cannot be ensured. This, too, is a factor which prevents the location of the structure of the pivotal connection section from being made closer to the inner surface of the cavity in the bendable tube.

Moreover, in the conventional structure, since the rivet-like shaft pin for connecting both the overlapped ear portions is fixed by caulking, the strength of retention of the shaft pin is relatively low. In order to ensure strength for preventing removal, there is a need to increase the diameter of the insertion hole for pivotal connection and the diameter of the shaft pin. Consequently, it is required to increase the width of the ear portion and the diameter of the shaft pin. Accordingly, the entire pivotal connection section becomes larger and this prevents the location of the structure of the pivotal connection section from being made closer to the inner surface of the cavity in the bendable tube.

Besides, since the shaft pin is of the rivet type and requires fixation by caulking, the assembling process therefor is time-consuming.

The above problems are common to all endoscopes. In the case of an endoscope with a small-diameter insertion section, however, the width and thickness of the ear portion are smaller and these problems become more serious.

BRIEF SUMMARY OF THE INVENTION

The object of the present invention is to provide a bendable tube of an endoscope, wherein a structural part of a pivotal connection section for connecting adjacent joint rings is reduced in size and the strength of connection is increased, and the structural part of the pivotal connection section can be situated closer to an inner surface of an inner cavity in the bendable tube, whereby the diameter of the bendable tube can be reduced.

In order to achieve the object, in a bendable tube of an endoscope according to the present invention, a plurality of joint rings each having a rotational axis perpendicular to a direction of bending of an insertion section of the endoscope are arranged in a longitudinal direction of the insertion section, and adjacent ones of the joint rings are rotatably connected by means of shaft members. Each shaft member comprises a small-diameter portion and a large-diameter portion. A rotary shaft hole, which has a diameter equal to or slightly greater than a diameter of the small-diameter portion, is formed in one of the adjacent joint rings which are rotatably connected. An end face of the small-diameter portion of the shaft member is fitted in the rotary shaft hole and fixed to the other joint ring by integral connection means.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

First Embodiment

Figure 1A:
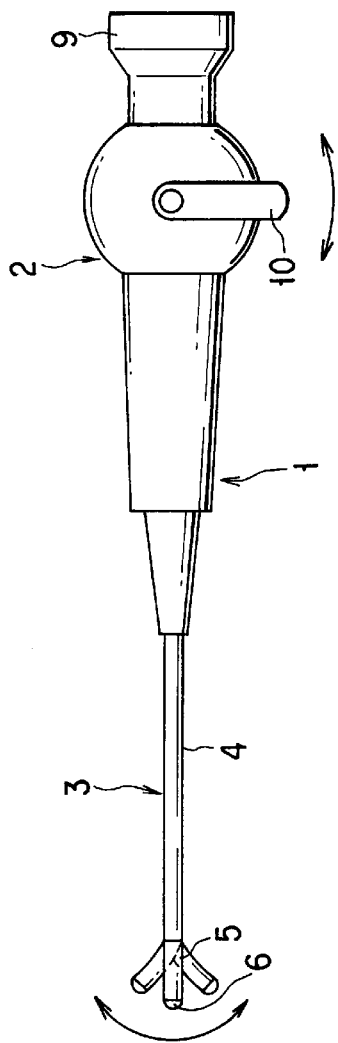
FIG. 1A schematically shows the entirety of an external structure of an endoscope according to a first embodiment of the invention.

An endoscope according to a first embodiment of the present invention will now be described with reference to FIGS. 1A to 6. FIG. 1A schematically shows the entire structure of an endoscope 1 with a small diameter such as an intrauterine endoscope. The endoscope 1 has a manipulation section 2 and an insertion section 3. The manipulation section 2 is provided with an eyepiece 9, an angle control knob 10, etc. The insertion section 3 comprises a resilient tube (resilient portion) 4, a bendable tube (bending portion) 5 and a distal portion 6. The bendable tube 5 is interposed between the resilient tube 4 located on the proximal-end side of the bendable tube 5 and the distal portion 6 located on the distal-end side of the bendable tube 5. The bendable tube 5 is bent up and down by means of a pair of upper and lower manipulation wire elements 7 and 8 by operating the angle control knob 10 of the manipulation section 2.

Figure 1B:
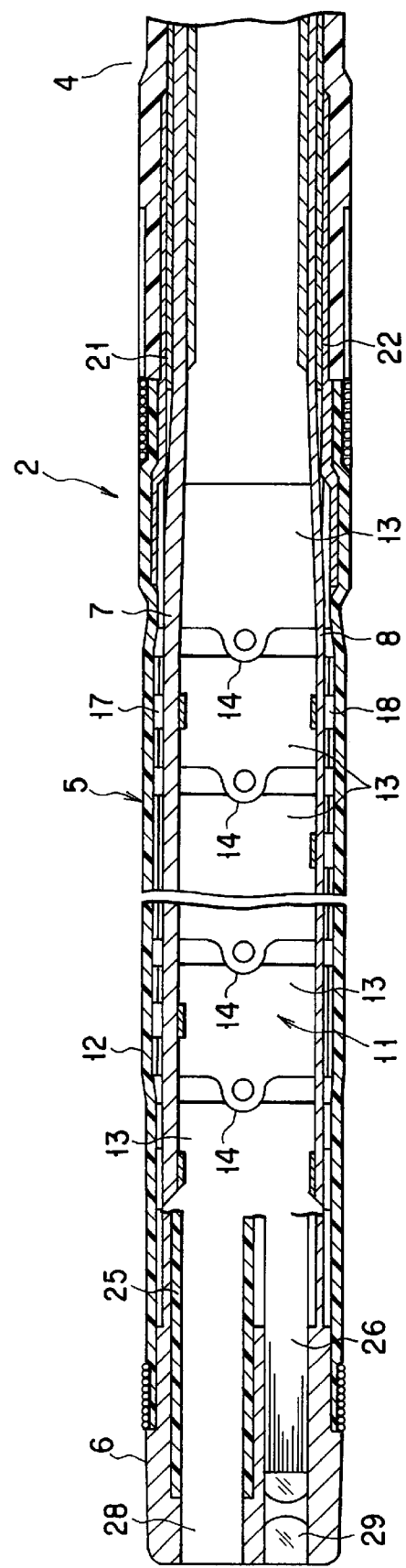
FIG. 1B is a vertical cross-sectional view of an insertion section of the endoscope.

FIG. 1B shows a specific structure of the region including the bendable tube 5 in the insertion section 3 of endoscope 1. The bendable tube 5 comprises a core member 11 and a sheath tube 12 surrounding the core member 11. The core member 11 has a plurality of metal joint rings 13 each having a short-tube shape. The joint rings 13 are arranged linearly in the longitudinal direction of the insertion section 3. A pair of right and left tongue portions (ear portions) 14 are provided at each of the front and rear ends of the joint rings 13 which adjoin one another. Each tongue portion 14 is integrally projected from an edge of the main body of the associated joint ring 13 in the longitudinal direction of the insertion section 3.

Figure 4:
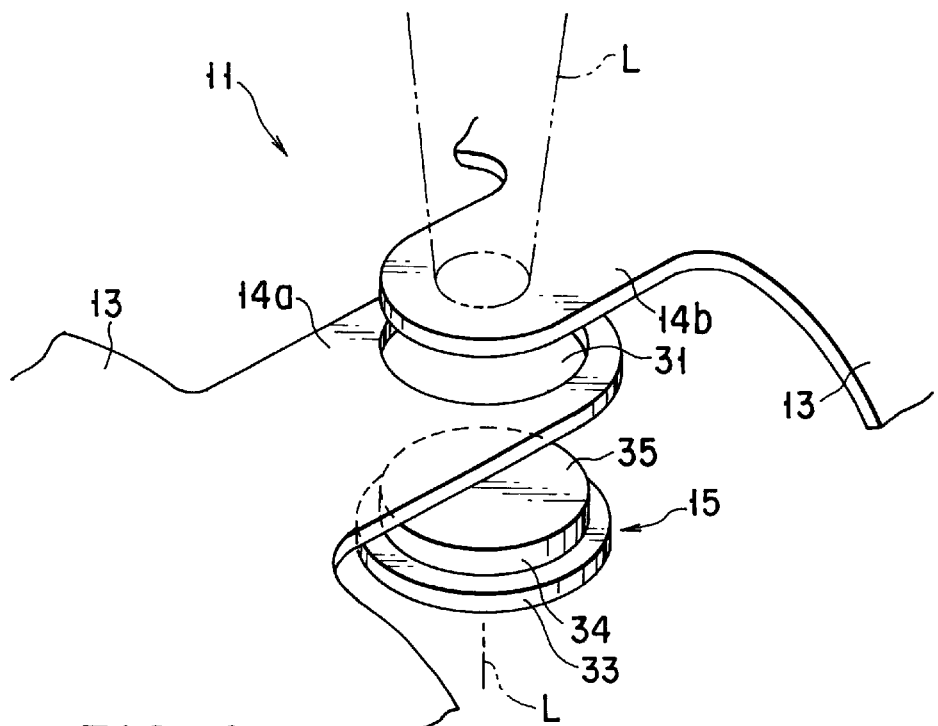
FIG. 4 is a developed perspective view of members constituting a pivotal connection section of joint rings of the bendable tube of the endoscope.
Figure 5:
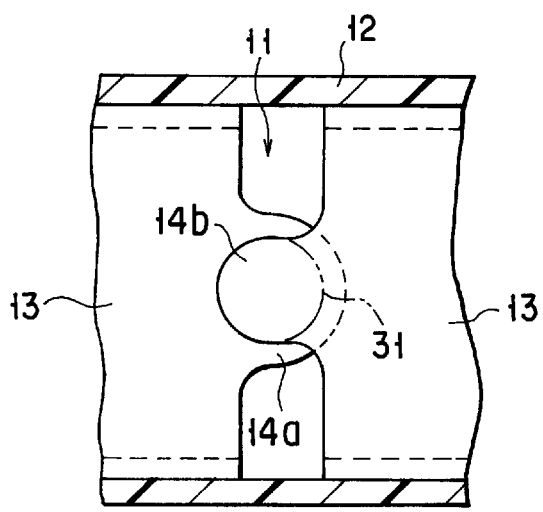
FIG. 5 is a vertical cross-sectional view of the pivotal connection section of the joint rings of the bendable tube of the endoscope.
Figure 6:
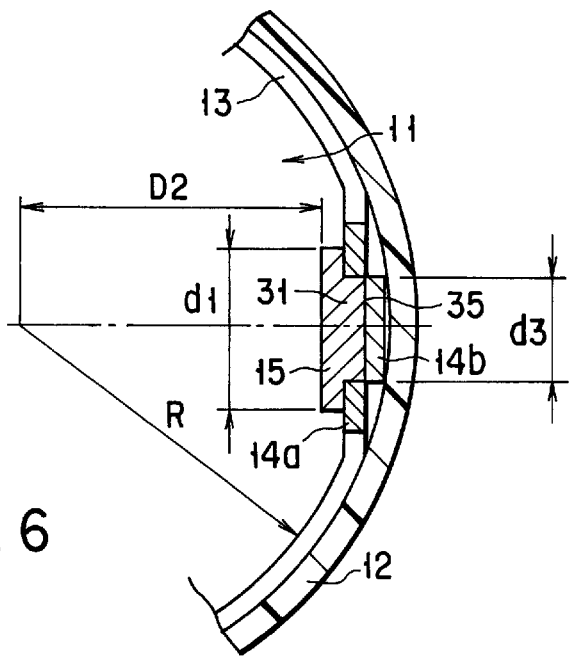
FIG. 6 is a transverse cross-sectional view of the pivotal connection section of the joint rings of the bendable tube of the endoscope.

As is shown in FIGS. 4 to 6, a rear-side tongue portion 14a of the joint ring 13 and a front-side tongue portion 14b of the joint ring 13, which is located on the front side of the rear-side tongue portion 14a, are connected such that distal end portions of these tongue portions 14a and 14b overlap each other. In this case, the front-side tongue portion 14a is located inside, and the rear-side tongue portion 14b is located outside. The overlapping tongue portions 14a and 14b are pivotally connected by means of a metal shaft member 15, as will be described below. By virtue of the pivotal connection section, the front and rear joint rings 13 can be connected vertically rotatable. Specifically, the tongue portions 14a and 14b constitute a connection section for pivotally connecting the adjoining joint rings 13.

As regards mutually opposed end portions of adjacent two joint rings 13, however, only one of the end portions may be provided with a projecting tongue portion 14, and this projecting tongue portion 14 may be overlapped with a connection portion which is formed of a portion of the main body of the mating joint ring 13.

No tongue portion is provided at the front end of the foremost joint ring 13. The front end portion of the foremost joint ring 13 is fixed to the distal portion 6. In addition, no tongue portion is provided at the rear end of the rearmost joint ring 13. The rear end portion of the rearmost joint ring 13 is fixed to a distal end portion of the resilient tube 4.

Figure 2:
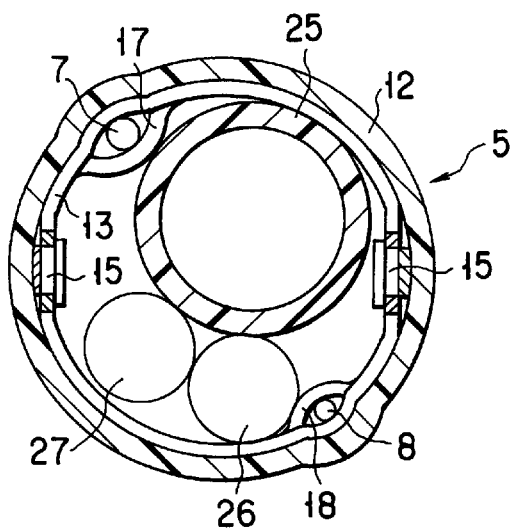
FIG. 2 is a transverse cross-sectional view of a bendable tube of the insertion section of the endoscope.

As is shown in FIG. 2, ring-shaped guide portions 17 and 18 for guiding the manipulation wire elements 7 and 8 are formed on the inner surface of each joint ring 13 by cutting out portions of the wall of the joint ring 13. The paired upper and lower manipulation wire elements 7 and 8 are individually passed through the upper guide portion 17 and lower guide portion 18. Thus, the manipulation wire elements 7 and 8 are situated at substantially upper and lower positions within the bendable tube 5. Distal end portions of the manipulation wire elements 7 and 8 are connected to the foremost joint ring 13. Proximal end portions of the wire elements 7 and 8 are guided to the manipulation section 2 through wire guide tubes 21 and 22 provided within the resilient tube 4 and are connected to an angle control mechanism (not shown) operated by the angle control knob 10.

The wire guide tubes 21 and 22 differ in thickness. The upper manipulation wire element 7 is thick and the lower manipulation wire element 8 is thin. The wire elements 7 and 8 are formed of the same material. The sizes of the guide portions 17 and 18 and wire guide tubes 21 and 22 are made different in accordance with the thickness of the associated manipulation wire elements 7 and 8.

For example, one of the manipulation wire elements 7 and 8, which is used to bend the bendable tube 5 over a larger angle in one direction, is made thicker. In the embodiment, the upper manipulation wire element 7 is made thicker to have a greater strength. Accordingly, the upper wire element 7 is capable of greatly bending the bendable tube 5 upward. On the other hand, the angle of downward bending of the bendable tube 5 may be made smaller.

Figure 3:
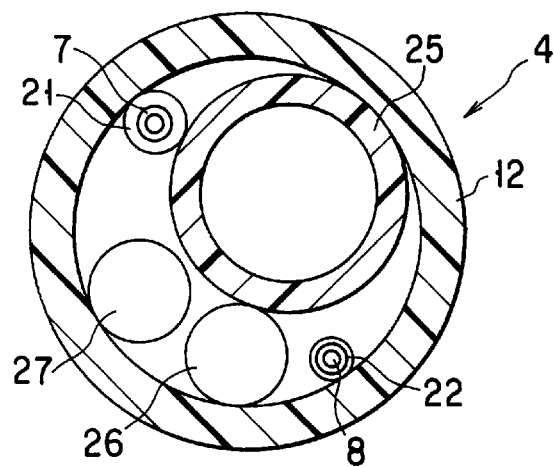
FIG. 3 is a transverse cross-sectional view of a resilient tube of the insertion section of the endoscope.

This designing is related to the operations of the endoscope and the internal members built within the endoscope. In this embodiment, the internal members are accommodated in the following manner. As is shown in FIGS. 2 and 3, a relatively thick forceps channel tube 25 is located upward, and an image guide fiber bundle 26 as well as a light guide fiber bundle 27 is located downward.

As is shown in FIG. 1B, a distal end portion of the forceps channel tube 25 is connected to a forceps 28 formed at the distal portion 6. In addition, distal end portions of the internal members such as the image guide fiber bundle 26 and light guide fiber bundle 27 are connected to the distal portion 6. The image guide fiber bundle 26 is connected to an objective lens 29 at the distal portion 6.

With reference to FIGS. 4 to 6, pivotal connection means for connecting tongue portions 14 of joint rings 13 of the bendable tube 5 will now be specifically described. The tongue portion 14a formed at the rear end of a forward one of the paired adjacent joint rings 13 is located inside the tongue portion 14b formed at the front end of the rearward joint ring 13. The width of the outside tongue portion 14b is less than that of the inside tongue portion 14a. The tongue portions 14a and 14b are plate-like members with the same thickness. The distal end portions of the tongue portions 14a and 14b overlap each other so that they may be connected. The tongue portions 14a and 14b are pivotally connected by means of the shaft member 15, as will be described later, so that the front and rear joint rings 13 may be vertically rotatably connected.

The projecting distal end portion of the inside tongue portion 14a has a semicircular arcuated shape, with its width being equal to its diameter. A circular insertion hole 31 forming a rotary shaft hole is made at a center of the projecting distal end portion of the tongue portion 14a. The shaft member 15 is fitted in the insertion hole 31 in a direction perpendicular to the longitudinal direction of the insertion section 3.

Although the outside tongue portion 14b is formed to have a width substantially equal to the diameter of the insertion hole 31, this width may be less. The projecting distal end portion of the tongue portion 14b is formed in a semicircular arcuated shape, with its width being equal to its diameter.

Figure 7:
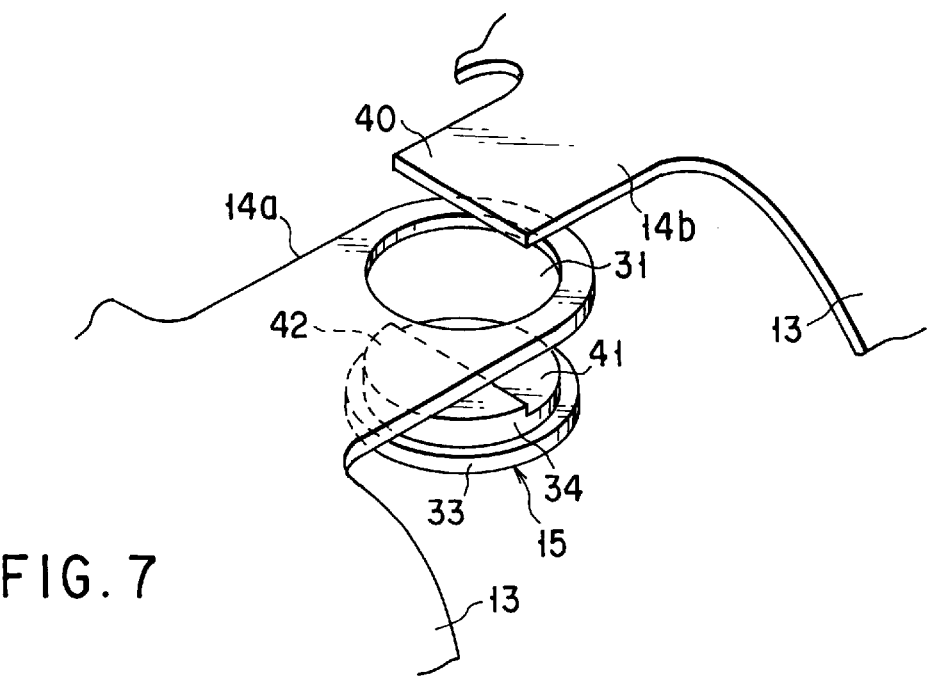
FIG. 7 is a developed perspective view of members constituting a pivotal connection section of joint rings of the bendable tube of the endoscope according to a second embodiment of the invention.

As is shown in FIGS. 4, 6 and 7, the shaft member 15 has an axis L and comprises a flange-like large-diameter portion 33 and a small-diameter portion 34. These portions 33 and 34 are integrally and coaxially formed of a metallic material. The large-diameter portion 33 is formed at one end of the axis L, and the small-diameter portion 34 is formed at the other end of the axis L. The outside diameter d1 of the large-diameter portion 33 is within the range of the width of the inside tongue portion 14a. The thickness of the large-diameter portion 33 is substantially equal to that of the tongue portion 14. The outside diameter of the small-diameter portion 34 is substantially equal to or less than the diameter d3 of the insertion hole 31. It is preferable that the height (width) of the small-diameter portion 34 of shaft member 15 be substantially equal to or greater than the thickness of the tongue portion 14 having the insertion hole 31. In addition, the projecting distal end portion of the outside tongue portion 14b is formed to have such a shape and a size that it substantially overlaps the insertion hole 31. The projecting distal end portion of the tongue portion 14b can be coincidently overlapped with a circular distal end face 35 of the small-diameter portion 34 of the shaft member 15 fitted in the insertion hole 31.

Although the large-diameter portion 33 is formed as a complete ring-shaped flange, the ring shape may not be complete if it can receive the inside tongue portion 14a. For example, the large-diameter portion 33 may be provided with partial projecting portions. In this case, the diameter of the large-diameter portion 33 may be understood as a diameter of an envelope circle passing through distal end portions of such projecting portions.

A process of connecting the tongue portions 14 of the joint rings 13 of bendable tube 5 will now be described.

The tongue portions 14a and 14b of the adjacent front and rear joint rings 13 are aligned to overlap each other, as shown in FIG. 4. The small-diameter portion 34 of shaft member 15 is fitted, from inside, into the insertion hole 31 of the inside tongue portion 14a. Then, the distal end portion of the outside tongue portion 14b is superposed on the distal end face 35 of the small-diameter portion 34.

Using some jig, the distal end portion of the outside tongue portion 14b is mechanically pressed on the distal end face 35 of the small-diameter portion 34 of shaft member 15. With this contact state maintained, a spot of a laser beam L is radiated within an area of the distal end portion of the outside tongue portion 14b.

In this case, two or more laser beam spots may be radiated within the area. In normal cases, the area for welding is from 0.3 mm to several mm, one spot is sufficient.

If the spot of the laser beam L is thus radiated on the distal end portion of the outside tongue portion 14b, the distal end portion of the outside tongue portion 14b is welded to the distal end face 35 of the small-diameter portion 34 of shaft member 15 which is in contact with the distal end portion of the outside tongue portion 14b. Thus, a fixed portion is formed. FIGS. 5 and 6 show this assembled state.

Specifically, the shaft member 15 is integrally welded to the outside tongue portion 14b, and both are firmly fixed. The inside tongue portion 14a is clamped between the peripheral portion of the large-diameter portion 33 of shaft member 15 and a proximal portion of the outside tongue portion 14b, and removal of the shaft member 15 is prevented. More specifically, since the inside tongue portion 14a is clamped between the peripheral portion of the large-diameter portion 33 of shaft member 15 and the proximal portion of the outside tongue portion 14b, removal of the inside tongue portion 14a is prevented. In this state, the tongue portions 14a and 14b are pivotally connected by the shaft member 15.

According to this pivotal connection structure, compared to the conventional rivet-type connection method, projection of a head portion does not occur and a compact pivotal connection section for the tongue portions 14a and 14b can be constituted. In particular, since no portion projects beyond the thickness of the outside tongue portion 14b, the structural part of the pivotal connection section can be situated closer to the inner surface of the inner cavity of the bendable tube 5. Thus, the diameter of the bendable tube 5 can be reduced, and projection to the inner cavity in the bendable tube 5 can be prevented as much as possible. Moreover, since the width of the outside tongue portion 14b can be reduced, the outside tongue portion 14b can be situated near the inner surface of the inner cavity and shifted outward.

Unlike the prior art, the rivet is not used and the process for assembly is easy. Since the shaft member 15 is welded and integrally fixed to one of the paired tongue portions, 14b, the prevention of removal of the shaft member 15 is more ensured than in the prior art and the strength of the pivotal connection section can be increased.

In the conventional rivet-type method, the shaft pin is prevented from being removed and both tongue portions 14a and 14b are held by means of the caulked portion of the rivet. However, the area of the caulked portion is small and the caulked portion is easily broken. These problems are solved by the present invention. In the rivet-type method, there is non-uniformity in caulking force and proper processing is difficult. According to the structure of the present invention, however, the process for assembly is easy and the stable pivotal connection function can be easily achieved. Furthermore, since there is no need to provide one of the tongue portions, 14b, with the insertion hole for the shaft member 15, the manufacturing step for this can be omitted and the manufacturing cost can be reduced. The mechanical strength of the tongue portion 14b itself can be increased.

Second Embodiment

Figure 8:
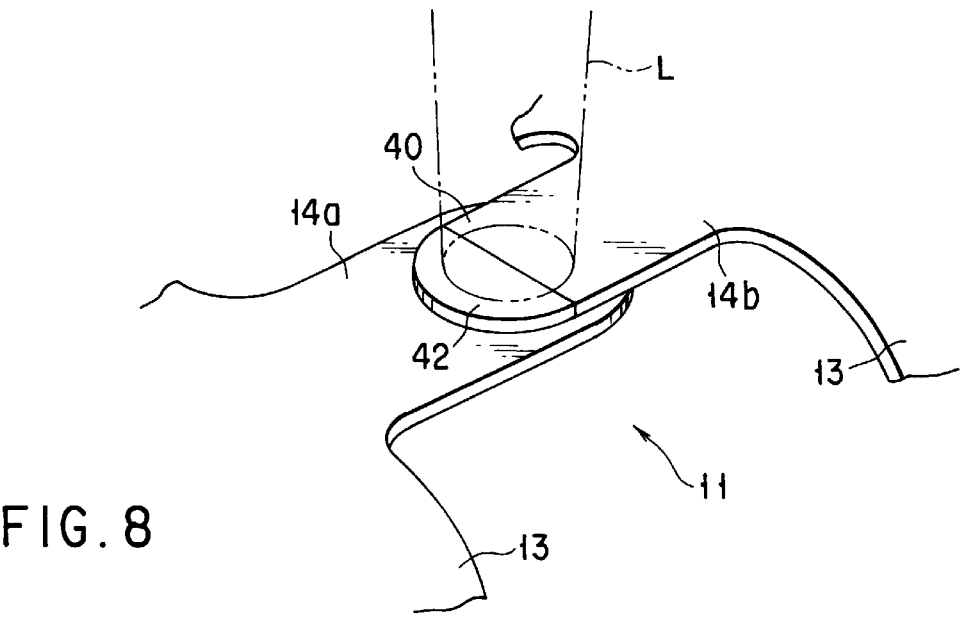
FIG. 8 is a perspective view of the pivotal connection section of the joint rings in the second embodiment.
Figure 9:
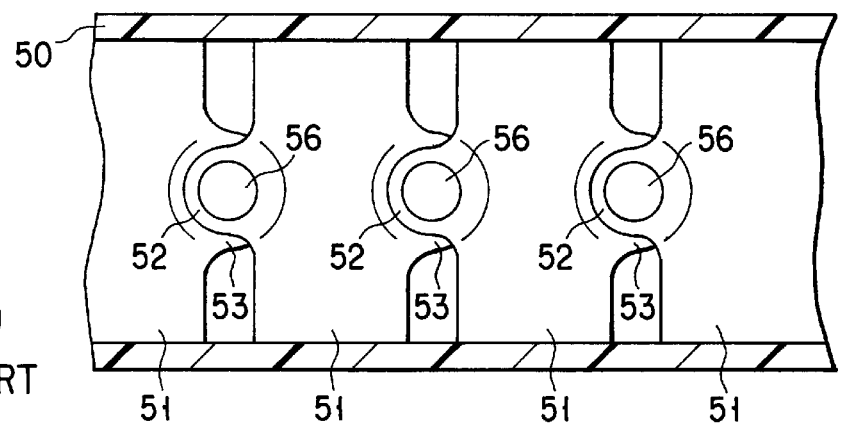
FIG. 9 is a vertical cross-sectional view of a bendable tube of an insertion section of a conventional endoscope.
Figure 10:
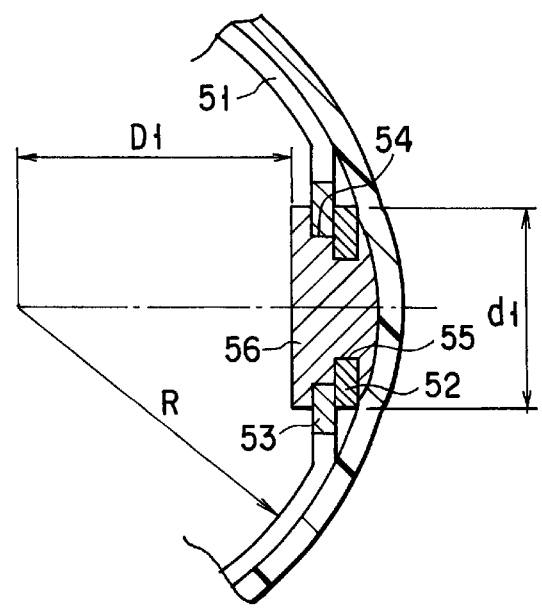
FIG. 10 is a transverse cross-sectional view of the bendable tube of the insertion section of the conventional endoscope.

Referring to FIGS. 7 and 8, a second embodiment of the present invention will now be described. The second embodiment relates to a modification of the pivotal connection means for connecting the tongue portions 14a and 14b of the joint rings 13 of bendable tube 5. Since the second embodiment includes structural parts substantially similar to those in the first embodiment, different portions will mainly be described.

The width of the outside tongue portion 14b is the same as in the first embodiment, but its distal end portion has a rectangular shape. A front end 40 of the distal end portion is linear.

On the other hand, a distal end portion of the small-diameter portion 34 of shaft member 15 is divided into a pair of semicircular surface portions which are stepped at a portion extending through the center of the distal end portion of the small-diameter portion 34. A height from a first surface portion 41 to a second surface portion 42 is substantially equal to the thickness of the outside tongue portion 14b. A height to the first surface portion 41 of the small-diameter portion 34 of shaft member 15 is substantially equal to or slightly greater than the thickness of the inside tongue portion 14a in which the insertion hole 31 is formed.

As is shown in FIG. 8, the front end 40 of outside tongue portion 14b is abutted upon the wall of the stepped portion, and the distal end portion of the tongue portion 14b is put in contact with the first surface portion 41. In this state, the laser beam L is radiated within the area of the distal end portion of the outside tongue portion 14b and the second surface portion 42 of the small-diameter portion 34 of shaft member 15. The distal end portion of the outside tongue portion 14b is thus welded to the distal end portion of the small-diameter portion 34 of shaft member 15. The degree of welding by the laser beam can be recognized by the eye. If welding is completely performed, the boundary along the stepped portion becomes hardly visible or disappears. In the assembling process, the alignment between the tongue portions 14a and 14b is easy.

The present invention is applicable not only to the endoscopes according to the above-described embodiments, but also to electronic endoscopes, medical treatment endoscopes, industrial endoscopes, etc. As regards the connecting means, the end face of the small-diameter portion of the shaft member and the tongue portion, which are to be integrally connected, may be put in surface-contact and welded or adhered. An ultraviolet-curing adhesive may be used as an adhesive.

As has been described above, according to the present invention, the pivotal connection section can be made compact, compared to the conventional rivet-type assembling method. In particular, the structural part of the pivotal connection section can be situated closer to the inner surface of the inner cavity in the bendable tube. Accordingly, the diameter of the bendable tube can be reduced and the projection to the inner cavity can be prevented as much as possible.

Since the caulking with the rivet is not used, the assembling process is simplified. Since the shaft member is fixed to the connection portion of one of the paired joint rings by connection means such as welding, removal of the shaft member is more ensured, compared to the conventional rivet-type method. At the same time, the strength of the pivotal connection section can be increased.

Furthermore, in the rivet-type method, there is non-uniformity in caulking force and proper processing is difficult. According to the structure of the present invention, however, the process for assembly is easy and the stable pivotal connection function can be easily achieved. Furthermore, since there is no need to provide one of the tongue portions, 14b, with the insertion hole for the shaft member 15, the manufacturing step for this can be omitted and the manufacturing cost can be reduced. The mechanical strength of the connection section can be increased.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A bendable tube of an endoscope, comprising:

a shaft member having a small-diameter portion and a larger-diameter portion;

at least one pair of adjacent first and second joint rings which are arranged linearly in a longitudinal direction of an insertion section of the endoscope and which are rotatably connected together;

wherein the first joint ring is provided with a rotary shaft hole having a diameter equal to or slightly greater than a diameter of the small-diameter portion of the shaft member and smaller than a diameter of the larger-diameter portion of the shaft member; and wherein the small-diameter portion of the shaft member is fitted in the rotary shaft hole in said first joint ring, and an end face of the small-diameter portion of the shaft member is fixed to a surface of the second joint ring.

2. A bendable tube of an endoscope according to claim 1, wherein mutually opposed end portions of said adjacent first and second joint rings are provided with tongue portions that overlap each other, and wherein the rotary shaft hole is formed in the tongue portion of said first joint ring and the end face of the small-diameter portion of the shaft is fixed to a surface of the tongue portion of said second joint ring.

3. A bendable tube of an endoscope according to claim 2, wherein the end face of the small-diameter portion of the shaft member is first put in surface-contact with and then fixed to the tongue portion of said second joint ring.

4. A bendable tube of an endoscope according to claim 2, wherein a width of the tongue portion of said second joint ring is substantially equal to or less than a diameter of the small-diameter portion of the shaft member.

5. A bendable tube of an endoscope according to claim 2, wherein the tongue portion of said first joint ring is situated inside the tongue portion of said second joint ring.

6. A bendable tube of an endoscope according to claim 1, wherein the end face of the small-diameter portion of the shaft member is fixed to the surface of said second joint ring by welding.

7. A bendable tube of an endoscope according to claim 2, wherein the end face of the small-diameter portion of the shaft member comprises two end surface portions with a step therebetween, and wherein a lower one of the two end surface portions is fixed to the tongue portion of said second joint ring.

8. A bendable tube of an endoscope according to claim 7, wherein a height of the step is substantially equal to a thickness of the tongue portion of said second joint ring.

9. An endoscope according to claim 1, wherein a height of said small-diameter portion of the shaft member is equal to or slightly greater than a thickness of said first joint ring.

10. A bendable tube of an endoscope, comprising:
- a shaft member having a small-diameter portion and a larger-diameter portion;
- at least one pair of adjacent first and second joint rings which are arranged linearly in a longitudinal direction of an insertion section of the endoscope and which are rotatably connected together;

wherein the first joint ring is provided with a rotary shaft hole having a diameter equal to or slightly greater than a diameter of the small-diameter portion of the shaft member and smaller than a diameter of the larger-diameter portion of the shaft member; and wherein the small-diameter portion of the shaft member is fitted in the rotary shaft hole in said first joint ring, and an outward end face of the small-diameter portion of the shaft member is fixed to an inward surface of the second joint ring.

* * * * *